US008875957B2

(12) United States Patent
Ho

(10) Patent No.: US 8,875,957 B2
(45) Date of Patent: Nov. 4, 2014

(54) SEALING CAP AND LIQUID STORAGE DEVICE USING THE SAME

(71) Applicant: Mu-Han Ho, Taichung (TW)

(72) Inventor: Mu-Han Ho, Taichung (TW)

( * ) Notice: Subject to any disclaimer, the term of this patent is extended or adjusted under 35 U.S.C. 154(b) by 1 day.

(21) Appl. No.: 13/798,731

(22) Filed: Mar. 13, 2013

(65) Prior Publication Data

US 2014/0166702 A1    Jun. 19, 2014

(30) Foreign Application Priority Data

Dec. 19, 2012 (TW) .............................. 101224581 A

(51) Int. Cl.
*B65D 25/46* (2006.01)
*B65D 37/00* (2006.01)
*B05B 11/04* (2006.01)
*B65D 51/18* (2006.01)

(52) U.S. Cl.
CPC .............. *B65D 37/00* (2013.01); *B05B 11/047* (2013.01); *B65D 51/18* (2013.01)
USPC ............................ 222/530; 222/538; 222/562

(58) Field of Classification Search
CPC .. B65D 47/2018; F16K 99/0026; F16K 7/068
USPC ......... 222/530, 538, 205, 562, 211, 206, 534; 422/100; 251/4, 9; 239/16; 220/252, 220/780, 810
See application file for complete search history.

(56) References Cited

U.S. PATENT DOCUMENTS

| 187,561 | A | * | 2/1877 | Rightor | 222/530 |
| 470,776 | A | * | 3/1892 | Beehler | 222/529 |
| 672,207 | A | * | 4/1901 | Dunn | 604/299 |
| 937,311 | A | * | 10/1909 | Leyner | 604/212 |
| 1,336,891 | A | * | 4/1920 | Corbin | 251/4 |
| 1,548,956 | A | * | 8/1925 | Rosenberg | 222/189.07 |
| 1,589,056 | A | * | 6/1926 | Drummond | 222/394 |
| 2,002,835 | A | * | 5/1935 | Rose | 251/10 |
| 2,716,013 | A | * | 8/1955 | Tinker | 251/4 |
| 2,792,976 | A | * | 5/1957 | Hall | 222/569 |
| 2,957,614 | A | * | 10/1960 | Krajcovic | 229/103.1 |
| 2,995,334 | A | * | 8/1961 | Henderson et al. | 251/4 |
| 3,029,059 | A | * | 4/1962 | Hamilton et al. | 251/9 |
| 3,100,486 | A | * | 8/1963 | Nehring | 604/272 |
| 3,103,335 | A | * | 9/1963 | Martinez | 251/4 |
| 3,256,579 | A | * | 6/1966 | Eugene | 24/134 R |
| 3,330,526 | A | * | 7/1967 | Berney | 251/9 |
| 4,080,989 | A | * | 3/1978 | Chapelsky et al. | 137/588 |
| 4,138,040 | A | * | 2/1979 | Stock | 222/420 |

(Continued)

*Primary Examiner* — Kevin P Shaver
*Assistant Examiner* — Michael J Melaragno
(74) *Attorney, Agent, or Firm* — Muncy, Geissler, Olds & Lowe, P.C.

(57) ABSTRACT

A sealing cap is formed of a bottom portion having a first chamber, a first axial opening, and a second axial opening, a cap portion having an opening end, a positionable end, and a second chamber, and a bendable portion integrally extending to an end edge of the opening end from an end edge of the first axial opening close to the cap portion and having a guide groove communicating with the first and second chambers. Besides, the bendable portion can be bended to make the cap portion be positioned to the bottom portion. When the sealing cap is sleeved onto an opening of a container having a flexible elongated tube, the bendable portion can be bended to force the flexible elongated tube for bending and to make the cap portion be positioned to the bottom portion, thus leading to preferable sealing effect.

12 Claims, 7 Drawing Sheets

(56) References Cited

U.S. PATENT DOCUMENTS

| | | | |
|---|---|---|---|
| 4,453,653 A * | 6/1984 | Chapelsky et al. | 222/528 |
| 4,453,696 A * | 6/1984 | Witt | 251/4 |
| 4,596,780 A * | 6/1986 | Castaneda | 436/176 |
| 4,611,785 A * | 9/1986 | Steer | 251/4 |
| 4,627,538 A * | 12/1986 | Kafkis | 206/524.1 |
| 4,925,128 A * | 5/1990 | Brody | 222/211 |
| 5,320,257 A * | 6/1994 | Snedden | 222/215 |
| 5,370,279 A * | 12/1994 | Tardif | 222/214 |
| 5,388,712 A * | 2/1995 | Brody | 215/229 |
| 5,460,782 A * | 10/1995 | Coleman et al. | 422/520 |
| 5,893,491 A * | 4/1999 | Brody | 222/530 |
| 6,131,775 A * | 10/2000 | Brody | 222/211 |
| 6,343,717 B1 * | 2/2002 | Zhang et al. | 222/209 |
| 6,666,354 B2 * | 12/2003 | Hudson et al. | 222/147 |
| 2006/0016478 A1 * | 1/2006 | Chantalat | 137/223 |
| 2006/0196895 A1 * | 9/2006 | Trejo | 222/528 |
| 2008/0292505 A1 * | 11/2008 | Tian | 422/100 |

* cited by examiner

SEALING CAP AND LIQUID STORAGE DEVICE USING THE SAME

BACKGROUND OF THE INVENTION

1. Field of the Invention

The present invention relates generally to a sealing cap and more particularly, to a flexible sealing cap and a liquid storage device using the same.

2. Description of the Related Art

A container having a flexible long tube is frequently used at many places in daily life for dispensation, collection, and storage of various liquids.

Taking a long-spouted bottle as an example, it is usually used for storage of lubricating oil, salad oil, sauce, paste, or ink and when it not in use, its cap is directly sleeved onto its flexible tubular portion to seal the opening of the flexible tubular portion. However, such cap fails to seal the opening perfectly because when such long-spouted bottle is put upside-down or deforms subject to thermal expansion and contraction, the fluid inside the bottle tends to leak from the opening.

In addition, a urine test tube or urine bottle for collecting a patient's urine in the hospital is instanced as a general container in need of frequent dispensation and having a sealing cap. When it intended to collect the urine, the patient needs to pass the urine into a paper cup and then pour the urine into the aforesaid urine test tube or urine bottle from the paper cup. However, such manner may lead to spill of the urine to the patient's hand in the process of pouring the urine because the opening of the urine test tube or urine bottle is too small, so it is inconvenient to collect the urine. Besides, the soft sealing cap of the urine test tube is subject to burst resulting from refrigeration and into leakage of the urine, and the spiral sealing cap of the urine bottle is provided with worse sealing effect. Furthermore, either of the urine test tube and the urine bottle is relatively high-cost and whenever the test proceeds, it is necessary to draw the urine by a dropper, thus not only wasting the dropper but likely polluting the urine sample.

In consideration of the aforesaid drawbacks, if a container capable of directly collecting, dispensing, and storing liquid at the same time, it will be more operationally convenient.

SUMMARY OF THE INVENTION

The primary objective of the present invention is to provide a sealing cap, which can seal a container having an elongated flexible tube effectively.

The foregoing objective of the present invention is attained by the sealing cap formed of a bottom portion, a cap portion, and a bendable portion. The bottom portion includes a first chamber, a first axial opening, and a second axial opening. The first and second axial openings are opposite to each other and communicate with the first chamber. The cap portion includes an opening end, a positionable end, and a second chamber. The positionable end is opposite to the opening end. The second chamber is located between the opening end and the positionable end. The bendable portion integrally extends to an end edge of the opening end of the bottom portion from an end edge of the first axial opening of the cap portion and includes a guide groove communicating with the first chamber and the second chamber. Besides, the bendable portion can be externally forced for deformation to make the cap portion move toward the bottom portion and then be positioned to the bottom portion. When a user sleeves the sealing cap onto an opening of a container having a flexible tube, the bendable portion can be bent to force the flexible tube for bending and to make the cap portion be positioned to the bottom portion, thus leading to preferable sealing effect.

The secondary objective of the present invention is to provide a liquid storage device, which can collect a liquid directly and release the liquid directly while it is required. In this way, while the liquid is collected or dispensed, the user's hand will not be polluted, the cost is relatively lower, and it can prevent the liquid in storage inside the liquid storage device from pollution. Besides, the sealing cap can effectively seal the liquid storage device to prevent the liquid in storage inside the liquid storage device from leakage.

The liquid storage device is formed of the aforesaid sealing cap and a liquid collector. The liquid collector includes a push portion, a flexible portion, and a bendable portion located between the push portion and the flexible portion. The push portion includes a chamber. The flexible portion and the bendable portion jointly have a flow channel communicating with the chamber. The flexible portion includes an opening communicating with the flow channel. The push portion can be resiliently deformed by an external force to make a gas inside the chamber flow through the flow channel and exhaust through the opening, and when the external force vanishes, the push portion can resiliently recover to make the liquid in contact with the opening be sucked into the flow channel to enter the chamber. The bendable portion is inserted through and into the first chamber and the first and second axial openings. The flexible portion is inserted into the second chamber.

In the sealing cap of a preferred embodiment of the present invention, the bottom portion includes a peripheral wall surrounding the first chamber. When the cap portion is moved toward the bottom portion, the positionable end of the cap portion is engaged into the first chamber to abut against the peripheral wall, so the positionable end is located between the peripheral wall and the bendable portion.

In addition, the bottom portion includes a slit communicating with the first axial opening or both of the first and second axial openings. The cap portion can be positioned to the bottom portion in a way that the positionable end passes through the slit to be engaged in the first chamber, so the positionable end is located between the peripheral wall and the bendable portion. Besides, the bottom portion becomes resilient due to the slot to be easily sleeved onto the bendable portion.

In the aforesaid preferred embodiment of the present invention, the cap portion is preferably taper-shaped where the cross-section of the opening end is larger than that of the positionable end, so the cap portion can be conveniently engaged into the first chamber.

In the sealing cap of a preferred embodiment of the present invention, the bottom portion includes a clip formed on a peripheral surface thereof and having a retaining portion. In this way, after the cap portion is moved toward the bottom portion, the positionable end can be engaged into the retaining portion to be positioned to the bottom portion.

DETAILED DESCRIPTION OF PREFERRED EMBODIMENTS

Structural features and desired effects of the present invention will become more fully understood by reference to two preferred embodiments given hereunder. However, it is to be understood that these embodiments are given by way of illustration only, thus are not limitative of the claim scope of the present invention.

Figure 1:
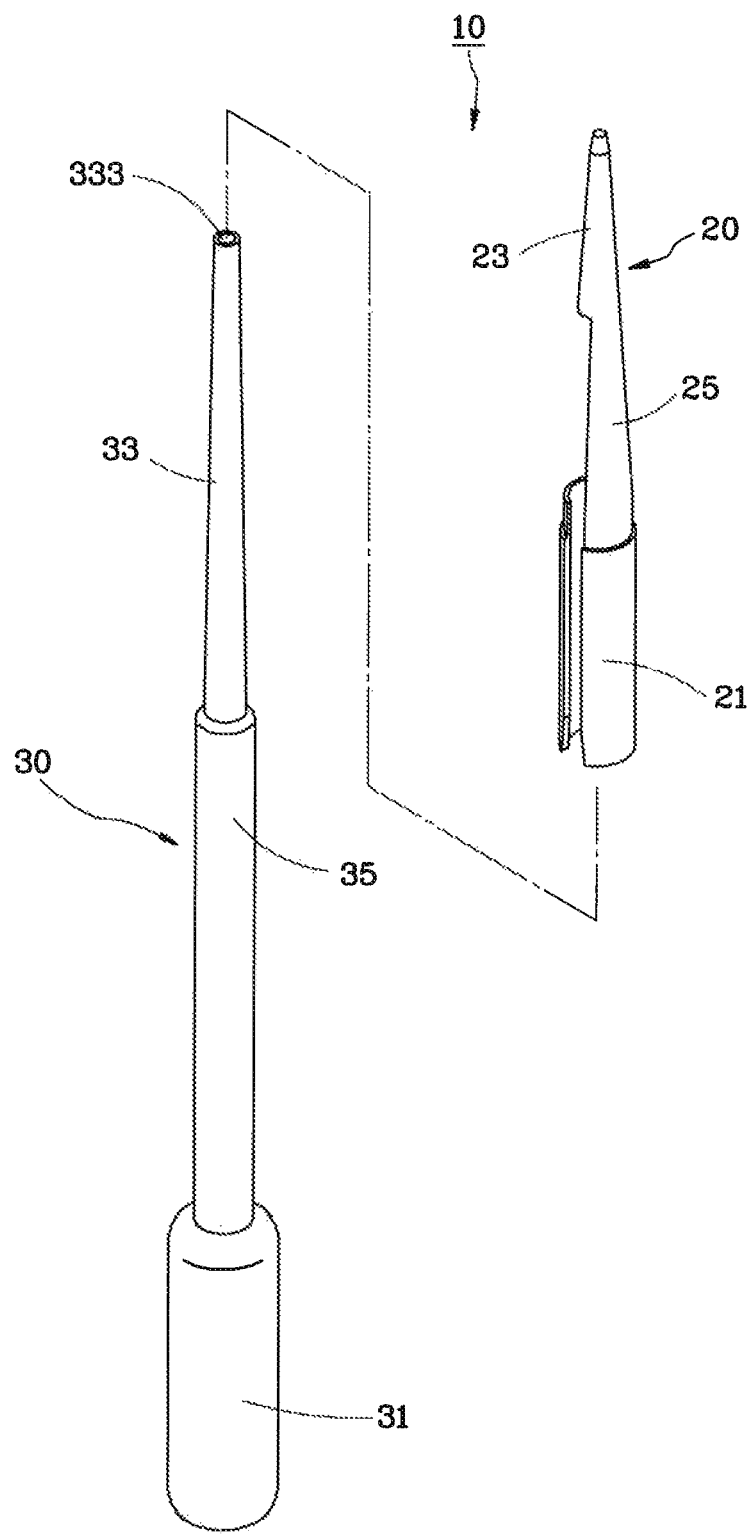
FIG. 1 is a perspective view of a first preferred embodiment of the present invention.

Referring to FIG. 1, a liquid storage device 10 constructed according to a first preferred embodiment of the present invention is formed of a sealing cap 20 and a liquid collector 30. The detailed descriptions and operations of these elements as well as their interrelations are recited in the respective paragraphs as follows.

Figure 2:
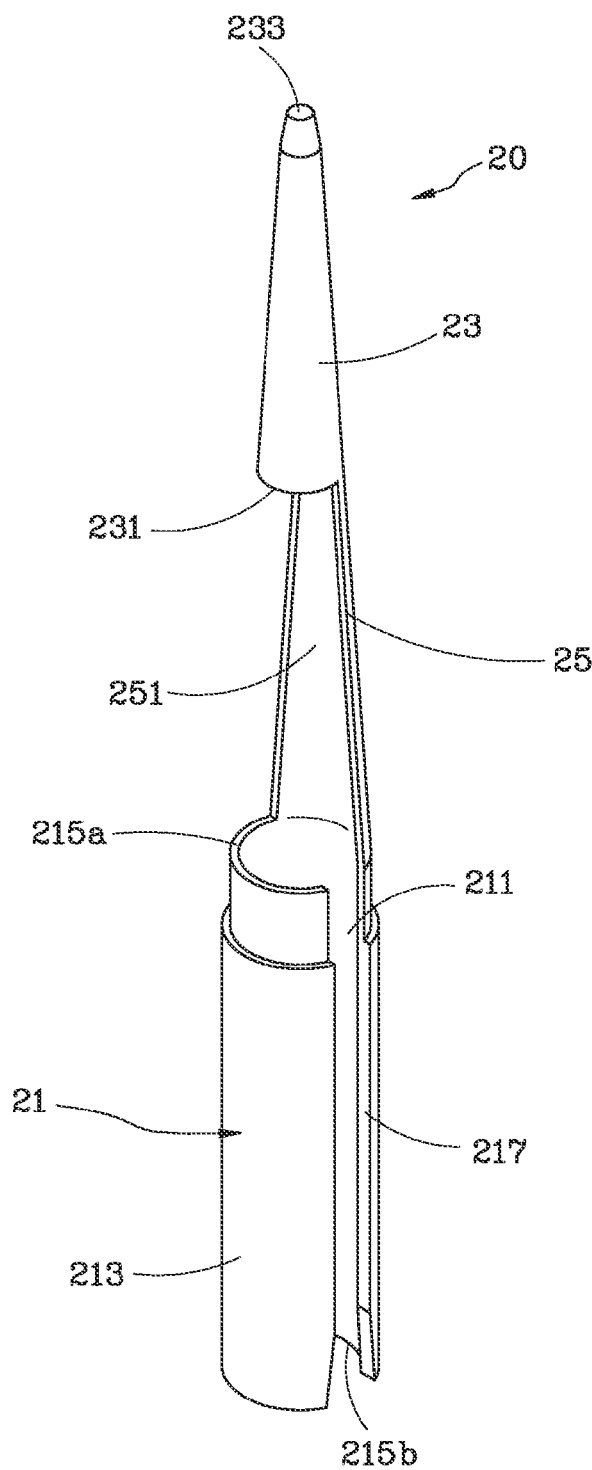
FIG. 2 is a perspective view of the sealing cap of the first preferred embodiment of the present invention.
Figure 3:
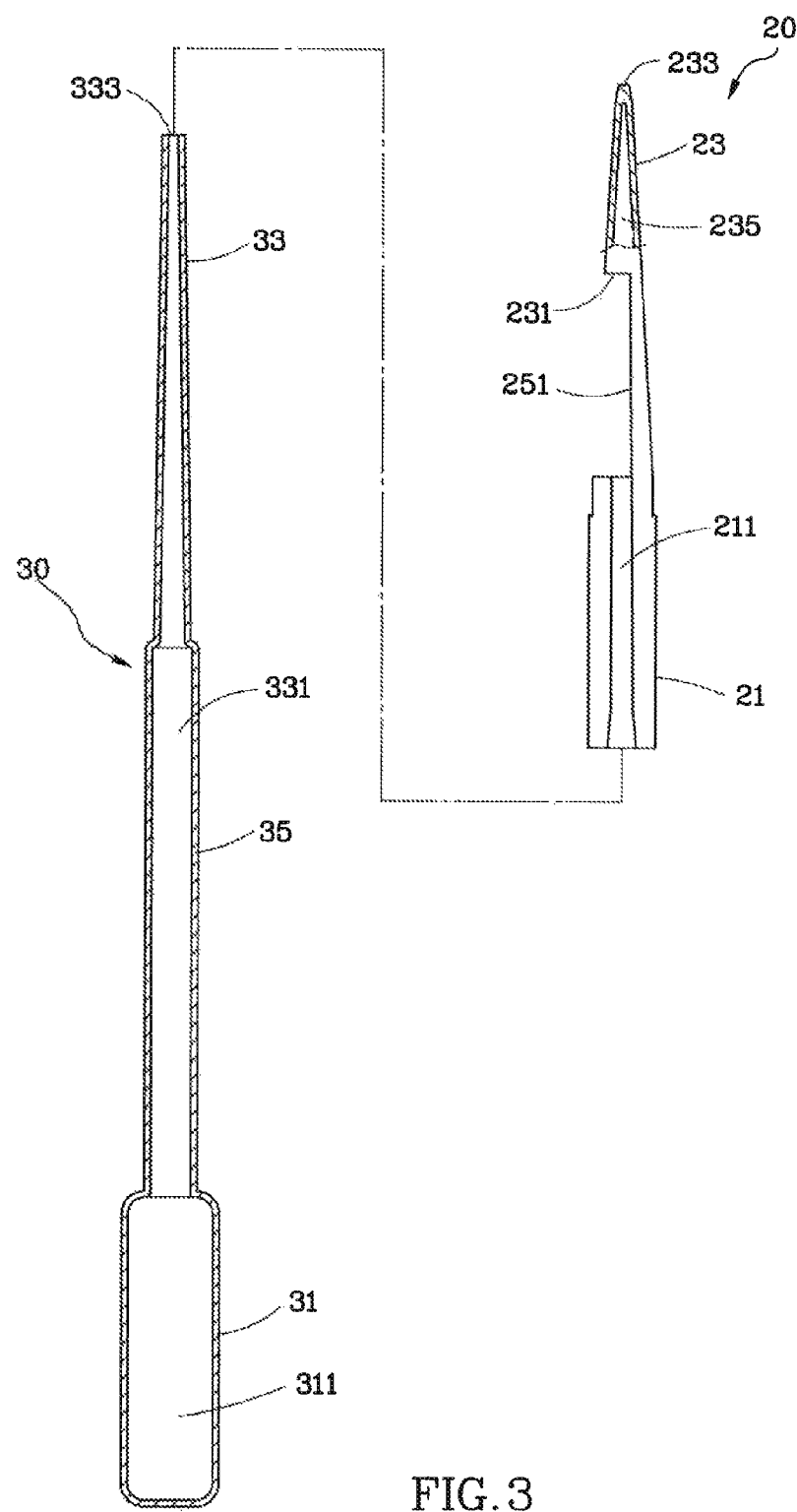
FIG. 3 is a sectional exploded view of the liquid storage device of the first preferred embodiment of the present invention.

Referring to FIG. 2, the sealing cap 20 includes a bottom portion 21, a cap portion 23, and a bendable portion 25. The bottom portion 21 is a tube in this embodiment and includes a first chamber 211, a peripheral wall 213 surrounding the first chamber 211, a first axial opening 215a, and a second axial opening 215b. The first and second axial openings 215a and 215b face each other and communicate with the first chamber 211. Besides, in this embodiment, the bottom portion 21 further includes a slit 217 communicating with the two axial openings 215a and 215b for making the bottom portion 21 be resilient to be easily sleeved onto a flexible elongated tubular container. As shown in FIGS. 2 and 3, the cap portion 23 includes an opening end 231, a positionable end 233, and a second chamber 235. The opening end 231 faces the first axial openings 215a. The second chamber 235 is located between the opening end 231 and the positionable end 233. The cap portion 23 is taper-shaped where the cross-section of the opening end 231 is larger than that of the positionable end 233. The bendable portion 25 is made of a flexible material and integrally extending to an end edge of the opening end 231 of the cap portion 23 from an end edge of the first axial opening 215a of the bottom portion 21 close to one of the axial openings 215a or 215b. The bendable portion 25 is provided with an arc-shaped cross-section to have a guide groove 251 communicating with the first and second chambers 211 and 235.

The liquid collector 30, as shown in FIGS. 1 and 3, is a dropper in this embodiment and includes a push portion 31, a flexible portion 33, and a body portion 35. The push portion 31, the flexible portion 33, and the body portion 35 are formed in one piece. The push portion 31 has a chamber 311. The flexible portion 33 has a flow channel 331 communicating with the chamber 311 and an opening 333 communicating with the flow channel 331.

In operation, the push portion 31 can be resiliently deformed by an external force and meanwhile, a gas inside chamber 311 can pass through the flow channel 331 and exhaust through the opening 333. When the external force vanishes, the push portion 31 resiliently recovers and in the meantime, suction is generated inside the flow channel 331, so a liquid in contact with the opening 333 can be sucked into the flow channel 331 to enter the chamber 311. In this way, when the liquid collector 30 is empty inside, the push portion 31 can be pushed to enable the liquid storage device 10 to collect the liquid directly. When it is intended to dispense the liquid, the push portion 31 can be pushed again to release the liquid directly through the opening 333 for dispensing the liquid.

It is particularly noted that the dropper is taken as an example of the liquid collector 30; however, the liquid collector 30 is not limited to the dropper and can be an alternative container having the push portion 31, the flexible portion 33, and the body portion 35, e.g. a long-spouted bottle. Besides, the wall surface of the body portion 35 can be alternatively provided with a scale for indicating the volume of liquid collected and released. The capacity of the push portion 31 can be variable, such as 10 ml, 20 ml, 30 ml, or 40 ml, subject to different usages.

Figure 4:
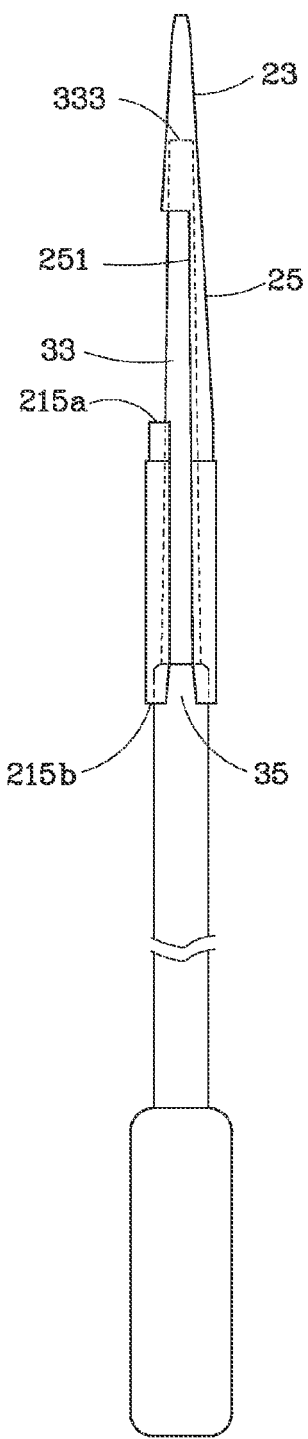
FIG. 4 is a schematic view of the first preferred embodiment of the present invention, illustrating that the liquid collector is not sealed.
Figure 5:
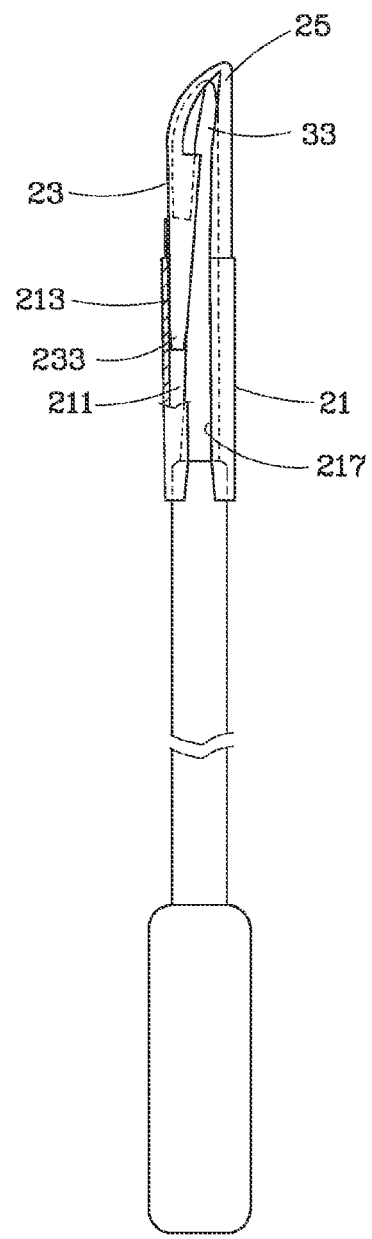
FIG. 5 is similar to FIG. 4, illustrating that the liquid collector is sealed.
Figure 6:
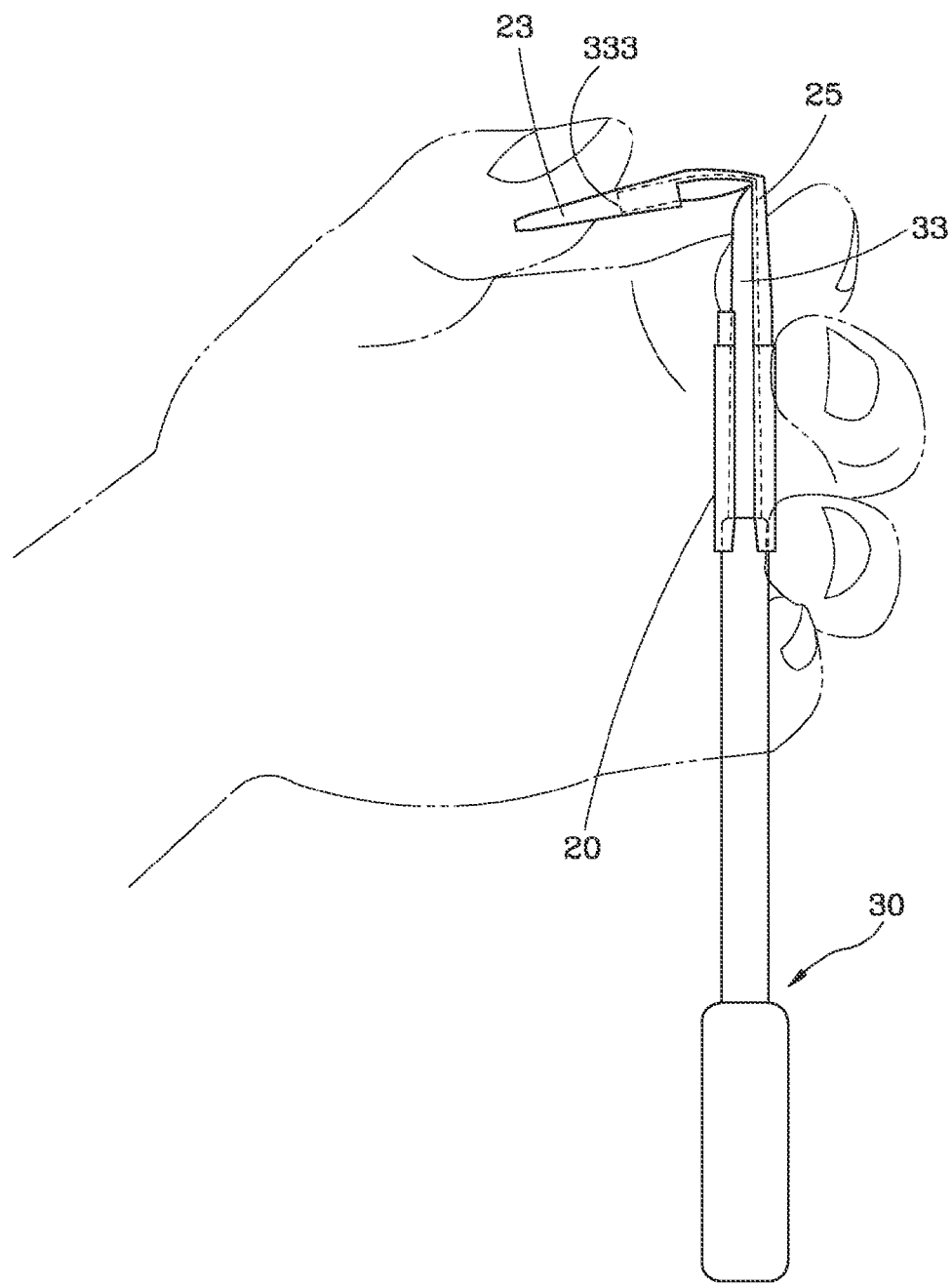
FIG. 6 is a schematic view of the first preferred embodiment of the present invention, illustrating that the user is bending the bendable portion by his or her hand to seal the liquid collector.

Referring to FIG. 4 and FIG. 3, when it is intended to seal the liquid storage device 30, the flexible portion 33 and the body portion 35 pass through the first and second axial openings 215a and 215b and the first chamber 211 to make the body portion 35 be located inside the first chamber 211; next, the flexible portion 33 can extend into the cap portion 23 along the guide groove 251 to make the opening 333 be located inside the second chamber 235. Referring to FIGS. 5-6, the user can apply an external force to the bendable portion 25 to force the bendable portion 25 and the flexible portion 33 to be bended to enable the positionable end 233 to move toward the bottom portion 21 and then the positionable end 233 is positioned to the bottom portion 21. In this embodiment, the cap portion 23 can be positioned to the bottom portion 21 by means of the peripheral wall 213 and the slit 217. In this way, the positionable end 233 of the cap portion 23 can pass through the slit 217 to be engaged into the first chamber 211 to abut against the peripheral wall 213 and to be located between the peripheral wall 213 and the body portion 35, so the cap portion 23 can be positioned to the bottom portion 21 and the liquid storage device 30 can be sealed.

It is worth mentioning that when the user proceeds with the aforesaid sealing operation, as shown in FIG. 6, the user's finger presses the cap portion 23 and the bendable portion 25, so it will unlikely happen that the collected liquid is polluted because the opening 333 of the liquid collector 30 or the flexible portion 33 are touched improperly.

Figure 7:
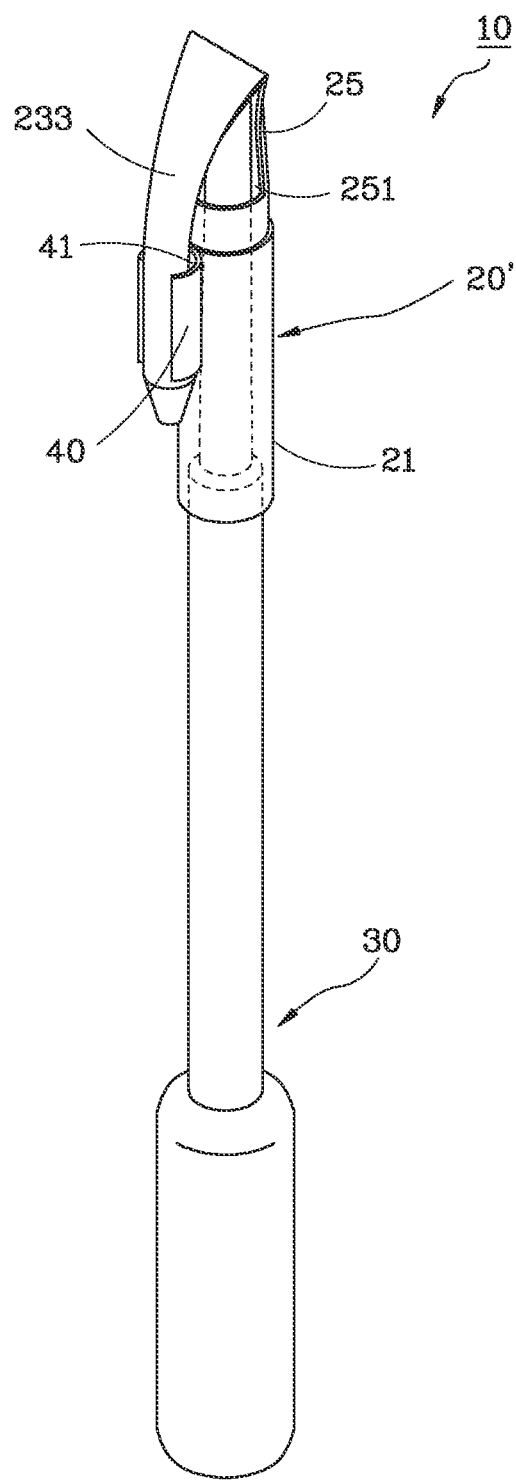
FIG. 7 is a schematic view of a second preferred embodiment of the present invention.

Referring to FIG. 7, a liquid storage device 10 constructed according to a second preferred embodiment of the present invention is similar to that of the first embodiment and the difference is specified hereinafter. The sealing cap 20' includes a clip 40 having a C-shaped cross-section and formed at an external peripheral surface of the bottom portion 21. The clip 40 is located at a corresponding position to the guide groove 251 and includes a retaining portion 41 having an opening facing a direction opposite to the bottom portion 21. In this way, the cap portion 23 can be engaged into the retaining portion 41 of the clip 40 to make the cap portion 23 be positioned to the bottom portion 21. In other words, the cap portion 23 can be positioned to the bottom portion 21 by the clip 40 in this embodiment.

Figure 8:
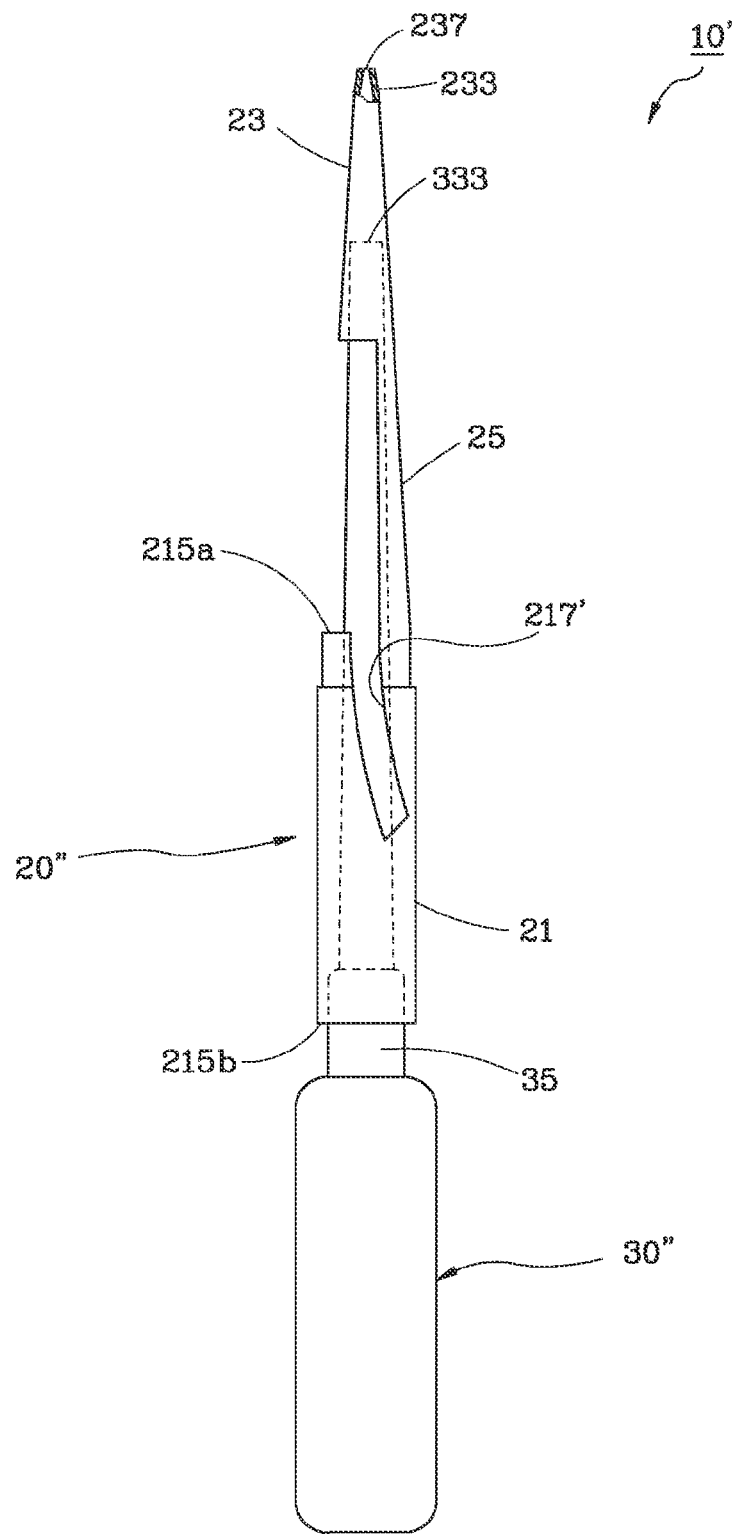
FIG. 8 is similar to FIG. 4, illustrating a third preferred embodiment of the present invention.

Referring to FIG. 8, a liquid storage device 10' constructed according to a third preferred embodiment of the present invention is similar to that of the first embodiment, having the following differences. In this embodiment, the bottom portion 21 of the sealing cap 20" includes a slit 217' communicating with the first axial opening 215a only. The positionable end 233 of the cap portion 23 includes an opening 237 running therethrough. The length of the body portion 35 of the liquid storage device 30" can be shortened to 1 cm subject to the actual need to reduce the volume as a whole. In this way, the user can bend the bendable portion 25 to make the positionable end 233 of the cap portion 23 pass through the slit 217' to be engaged into the first chamber 211 to further position the cap portion 23 to the bottom portion 21. When it is intended to use the liquid inside the chamber 311, the liquid can flow out of the opening 237 from the chamber 311 through the body portion 35 for convenience use in a way that the user pushes the push portion 31 after the positionable end 233 disengages from the bottom portion 21.

Because the sealing cap of the present invention can force the flexible portion of the liquid storage device or a flexible elongated tube of a container to be bended by bending the bendable portion and then the cap portion is positioned to the bottom portion, the sealing effect of the present invention is better than the prior art. Besides, the liquid storage device of the present invention can collect the liquid directly and release the liquid directly for its dispensation while it is needed, so the present invention includes the advantages of no pollution to the user's hand and to the liquid in storage and low production cost. Furthermore, the liquid storage device using the aforesaid seal cap can be effectively sealed to prevent the liquid in storage from leakage.

What is claimed is:

1. A sealing cap comprising:
    a bottom portion having a first chamber, a first axial opening, and a second axial opening, the first and second axial openings communicating with the first chamber;
    a cap portion having an opening end, a positionable end opposite to the opening end, and a second chamber located between the opening end and the positionable end;
    a bendable portion integrally extending to an end edge of the opening end from an end edge of one of the first axial opening close to the cap portion, the bendable portion having a guide groove communicating with the first and second chambers; and
    means for positioning the cap portion to the bottom portion after the bendable portion is bended.

2. The sealing cap as defined in claim 1, wherein the bottom portion comprises a peripheral wall surrounding the first chamber and the cap portion is positioned to the bottom portion in a way that the positionable end of the cap portion is located inside the first chamber and abuts against the peripheral wall.

3. The sealing cap as defined in claim 2, wherein the bottom portion comprises a slit communicating with the first axial opening or both of the first and second axial openings and the cap portion is positioned to the bottom portion in a way that the positionable end of the cap portion passes through the slit to be positioned inside the first chamber.

4. The sealing cap as defined in claim 1 further comprising a clip formed at an external peripheral surface of the bottom portion, wherein the clip has a retaining portion and the cap portion is positioned to the bottom portion in a way that the positionable end is engaged into the retaining portion of the clip.

5. The sealing cap as defined in claim 1, wherein the cap portion is taper-shaped where the cross-section of the opening end is larger than that of the positionable end.

6. The sealing cap as defined in claim 1, wherein, the positionable end of the cap portion comprises an opening communicating with the second chamber.

7. A liquid storage device comprising:
    a sealing cap defined in claim 1; and
    a liquid collector having a push portion, a flexible portion, and a body portion located between the push portion and the flexible portion, the push portion having a chamber, the flexible portion and the body portion jointly having a flow channel communicating with the chamber, the flexible portion having an opening communicating with the flow channel, the push portion of the liquid collector being resiliently deformable subject to an external force to enable a fluid inside the chamber to flow through the flow channel and to exhaust through the opening, the push portion being resiliently recoverable after the external force vanishes to enable another fluid in contact with the opening to be sucked into the flow channel to enter the chamber, the body portion being inserted into the first chamber and the first and second axial openings, the flexible portion being inserted into the second chamber.

8. The liquid storage device as defined in claim 7, wherein the bottom portion comprises a peripheral wall surrounding the first chamber and the cap portion is positioned to the bottom portion in a way that the positionable end of the cap portion is located inside the first chamber and abuts against the peripheral wall.

9. The liquid storage device as defined in claim 8, wherein the bottom portion comprises a slit communicating with the first axial opening or both of the first and second axial openings and the cap portion is positioned to the bottom portion in a way that the positionable end of the cap portion passes through the slit to be positioned inside the first chamber, so the positionable end is located between the peripheral wall and the body portion of the liquid collector.

10. The liquid storage device as defined in claim 7 further comprising a clip formed at an external peripheral surface of the bottom portion, wherein the clip has a retaining portion and the cap portion is positioned to the bottom portion in a way that the positionable end is engaged into the retaining portion of the clip.

11. The liquid storage device as defined in claim 7, wherein the cap portion is taper-shaped where the cross-section of the opening end is larger than that of the positionable end.

12. The liquid storage device as defined in claim 7, wherein the positionable end of the cap portion comprises an opening communicating with the second chamber.

\* \* \* \* \*